United States Patent
Miller (10) Patent No.: US 8,239,022 B2
(45) Date of Patent: Aug. 7, 2012

(54) METHODS AND SYSTEMS FOR DISCRIMINATING BETWEEN VENTRICULAR WAVEFORMS WHEN VENTRICULAR RATE EXCEEDS ATRIAL RATE

(75) Inventor: Andrew Miller, Redondo Beach, CA (US)

(73) Assignee: Pacesetter, Inc., Sylmar, CA (US)

( * ) Notice: Subject to any disclaimer, the term of this patent is extended or adjusted under 35 U.S.C. 154(b) by 766 days.

(21) Appl. No.: 12/356,420

(22) Filed: Jan. 20, 2009

(65) Prior Publication Data
US 2010/0185111 A1 Jul. 22, 2010

(51) Int. Cl.
*A61N 1/368* (2006.01)

(52) U.S. Cl. ............ 607/17; 607/15; 600/509; 600/510; 600/513; 600/519

(58) Field of Classification Search .................. 600/509, 600/510, 513, 519; 607/15, 17
See application file for complete search history.

(56) References Cited

U.S. PATENT DOCUMENTS

| 5,447,519 | A | 9/1995 | Peterson |
| 7,283,863 | B2 | 10/2007 | Gunderson et al. |
| 2003/0204215 | A1 | 10/2003 | Gunderson et al. |
| 2004/0015197 | A1 | 1/2004 | Gunderson |
| 2005/0256544 | A1* | 11/2005 | Thompson ...................... 607/14 |
| 2006/0095083 | A1* | 5/2006 | Zhang et al. .................... 607/14 |
| 2006/0217621 | A1* | 9/2006 | Kim et al. ...................... 600/509 |
| 2006/0224075 | A1 | 10/2006 | Gunderson et al. |
| 2008/0161870 | A1 | 7/2008 | Gunderson |

FOREIGN PATENT DOCUMENTS

| WO | 03092810 | A2 | 11/2003 |
| WO | 2004093974 | A2 | 11/2004 |
| WO | 2004093974 | A3 | 11/2004 |
| WO | 2006105391 | A1 | 10/2006 |

* cited by examiner

*Primary Examiner* — Joseph Dietrich (57) ABSTRACT

A ventricular rate based on first candidate waveforms and second candidate waveforms within sensed ventricular waveforms is compared to an atrial rate. If the ventricular rate exceeds the atrial rate, the first candidate waveforms and second candidate waveforms are compared to a ventricular polarization complex template to obtain a first morphology indicator and a second morphology indicator. If a morphology match inconsistency is present, the amount by which the ventricular rate exceeds the atrial rate is compared to a threshold. If the threshold is exceeded, high-ventricular-rate therapy to the heart is inhibited. The ventricular polarization complex template may be a QRS-complex template, in which case a match inconsistency is present if each of the first candidate waveforms and the second candidate waveforms do not match the QRS-complex template. Alternatively, the ventricular polarization complex template may be a T-wave template, in which case a match inconsistency is present if either of the first candidate waveforms and the second candidate waveforms matches the T-wave template.

8 Claims, 8 Drawing Sheets

METHODS AND SYSTEMS FOR DISCRIMINATING BETWEEN VENTRICULAR WAVEFORMS WHEN VENTRICULAR RATE EXCEEDS ATRIAL RATE

FIELD OF THE INVENTION

Embodiments of the present invention pertain generally to implantable medical devices, and more particularly to methods and systems that discriminate between ventricular waveforms, e.g., QRS waves and T waves, when a ventricular rate exceeds an atrial rate, so as to address possible T-wave oversensing.

BACKGROUND OF THE INVENTION

An implantable medical device is implanted in a patient to monitor, among other things, electrical activity of a heart and to deliver appropriate electrical therapy, as required. Implantable medical devices ("IMDs") include, for example, pacemakers, cardioverters, defibrillators, implantable cardioverter defibrillators ("ICD"), and the like. The electrical therapy produced by an IMD may include, for example, the application of stimulation pulses including pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to normal sinus rhythm.

Known IMDs monitor cardiac signals of a heart to determine if and when electrical therapy is needed to treat an arrhythmia. IMDs may track the rate or frequency of cardiac signal waveforms to determine if the rate of one or more waveforms of interest indicates an arrhythmia. For example, IMDs may calculate the rate at which ventricular waveforms of the heart occur. The ventricular waveforms may include QRS complexes and the rate at which the QRS complexes are detected is referred to as the ventricular heart rate. If the ventricular heart rate exceeds a predetermined threshold, the IMDs may determine that the heart is demonstrating symptoms of tachycardia. As a result, the IMDs may apply the electrical therapy to the heart to treat the detected tachycardia.

Known IMDs may, however, incorrectly calculate the rate at which QRS complexes occur. For example, the cardiac signals of some patients may include atypically large T-waves. The amplitude or size of these T-waves may be sufficiently large that known IMDs identify the T-waves as QRS complexes. As a result, the IMDs may count both a QRS complex and a T-wave in each cardiac cycle both as QRS complexes. If the IMDs count both the QRS complexes and T-waves in each cardiac cycle, the IMDs may incorrectly calculate the QRS complex as occurring twice as frequently as the QRS complex actually does occur. Consequently, the ventricular heart rate calculated by these IMDs may be twice as large as the actual ventricular heart rate. If the actual ventricular heart rate would not require the application of electrical therapy to treat tachycardia while the incorrectly calculated ventricular heart rate would require the therapy, the IMDs may unnecessarily apply electrical therapy.

Thus, a need exists for systems and methods for use with an IMD that discriminate between ventricular waveforms in order to determine a ventricular heart rate. Differentiating between the ventricular waveforms such as the QRS complexes and the T-waves may increase the accuracy in which the ventricular heart rates are calculated by IMDs and may reduce the potential for application of unnecessary electrical therapy to a non-tachycardic heart.

BRIEF SUMMARY OF THE INVENTION

A ventricular rate based on first candidate waveforms and second candidate waveforms within sensed ventricular waveforms is compared to an atrial rate. If the ventricular rate exceeds the atrial rate, the first candidate waveforms and second candidate waveforms are compared to a ventricular polarization complex template to obtain a first morphology indicator and a second morphology indicator. If a morphology match inconsistency is present, the amount by which the ventricular rate exceeds the atrial rate is compared to a threshold. If the threshold is exceeded, high-ventricular-rate therapy to the heart is inhibited. The ventricular polarization complex template may be a QRS-complex template, in which case a match inconsistency is present if each of the first candidate waveforms and the second candidate waveforms do not match the QRS-complex template. Alternatively, the ventricular polarization complex template may be a T-wave template, in which case a match inconsistency is present if either of the first candidate waveforms and the second candidate waveforms matches the T-wave template.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided that monitor cardiac signals of a heart to inhibit application of a stimulation pulse to the heart based on the monitored cardiac signals. The methods and systems may sense ventricular waveforms of interest of the heart, including the QRS complex and T-wave. If the ventricular waveforms of interest occur more frequently than the atrial waveforms of interest, then the morphology of the ventricular waveforms of interest may be compared to a waveform template. The comparison of the ventricular waveforms of interest to the template may reveal whether the heart is demonstrating tachycardia or whether one of the ventricular waveforms of interest is being double-counted. For example, the comparison may reveal that the T-waves of the heart are being counted as additional QRS complexes. If the waveform template more closely matches one of the ventricular waveforms of interest more than another ventricular waveform of interest, the methods and systems may inhibit or prevent application of a stimulation pulse to the heart in order to avoid an unnecessary shock to the patient.

Figure 1:
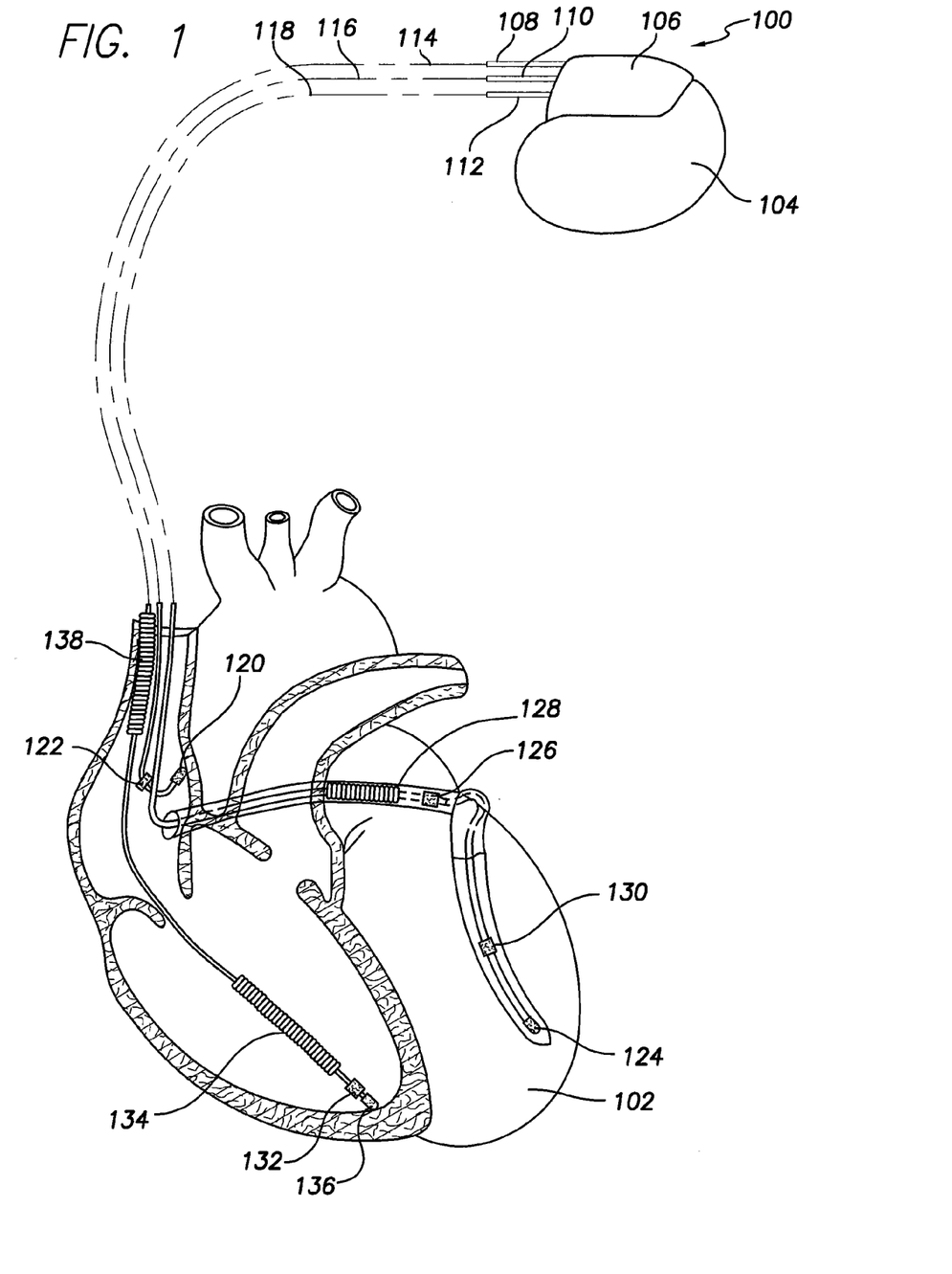
FIG. 1 illustrates an implantable medical device implemented in accordance with one embodiment and coupled to a heart in a patient.

FIG. 1 illustrates an IMD 100 implemented in accordance with one embodiment and coupled to a heart 102 in a patient. The IMD 100 may be a cardiac pacemaker, an ICD, a defibrillator, an ICD coupled with a pacemaker, and the like, implemented in accordance with one embodiment of the present invention. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 100 may be controlled to sense atrial and ventricular waveforms of interest, discriminate between two or more ventricular waveforms of interest and inhibit application of a stimulation pulse to a heart based on the discrimination between the waveforms of interest.

The IMD 100 includes a housing 104 that is joined to a header assembly 106 that holds receptacle connectors 108, 110, 112 connected to a right ventricular lead 114, a right atrial lead 116, and a coronary sinus lead 118, respectively. The leads 114, 116, and 118 measure cardiac signals of the heart 102. The right atrial lead 116 includes an atrial tip electrode 120 and an atrial ring electrode 122. The coronary sinus lead 118 includes a left ventricular tip electrode 124, a left atrial ring electrode 126, and a left atrial coil electrode 128. The coronary sinus lead 118 also is connected with an LV ring electrode 130 disposed between the LV tip electrode 124 and the left atrial ring electrode 126. The right ventricular lead 114 has an RV tip electrode 136, an RV ring electrode 132, an RV coil electrode 134, and an SVC coil electrode 138. The leads 114, 116, and 118 detect IEGM signals that form an electrical activity indicator of myocardial function over multiple cardiac cycles. Examples of waveforms identified from the IEGM signals include the P-wave, T-wave, the R-wave, the QRS complex, the ST segment, and the like.

Figure 2:
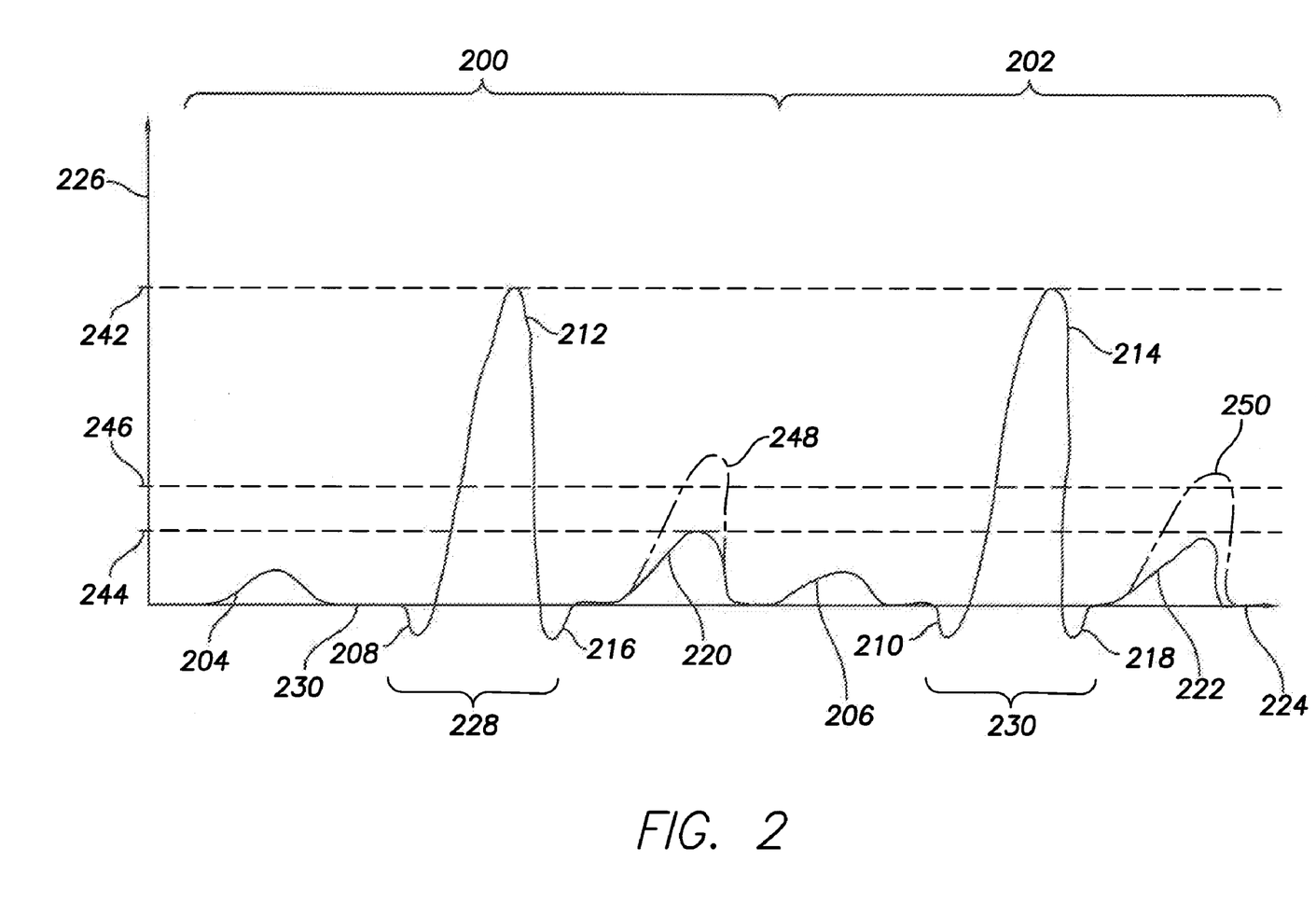
FIG. 2 illustrates examples of cardiac signals during two cardiac cycles.

FIG. 2 illustrates examples of cardiac signals during two cardiac cycles 200, 202. The horizontal axis 224 represents time, while the vertical axis 226 is defined in units of voltage. The cardiac signals include P-waves 204, 206, Q-waves 208, 210, R-waves 212, 214, S-waves 216, 218, and T-waves 220, 222. The P-waves 204, 206 represent atrial depolarization and may be used to characterize atrial activity of the heart 102. For example, the rate or frequency at which the P-waves 204, 206 appear during a predetermined time window may be used to identify a rate of atrial contraction, or an atrial heart beat ($A_{RATE}$). The QRS complexes 228, 230 in cardiac cycle 200, 202 is composed of the Q-waves 208, 210, the R-waves 212, 214, and the S-waves 220, 222. The QRS complexes 228, 230 correspond to the depolarization of the ventricles and may be used to characterize ventricular activity of the heart 102. For example, similar to the P-waves 204, 206, the QRS complexes 228, 230 may be used to identify a rate of ventricular contraction, or a ventricular heart beat ($V_{RATE}$). The T-waves 220, 222 represent the relaxation or repolarization of the ventricles and also may be used to characterize ventricular activity of the heart 102.

The QRS complexes 228, 230 may be used to locate the R-waves 212, 214 to determine a baseline 230. The baseline 230 is shown as being coextensive with the horizontal axis 224 in the illustrated embodiment, although the baseline may be located above or below the horizontal axis 224. The distance that the waves and complexes extend along the vertical axis 226 above the baseline 230 is representative of the amplitude of the waves and complexes. For example, a QRS amplitude 242 is the distance along the vertical axis 226 that the QRS complexes 238, 240 extend above the baseline 230. While the QRS amplitude 242 is illustrated as being the same for the two QRS complexes 228, 230 shown in FIG. 2, the amplitude 242 may vary between the QRS complexes 228, 230. A T-wave amplitude 244 is the distance along the vertical axis 226 that the T-waves 220, 222 extend above the baseline 230. While the T-wave amplitude 244 is the same for the T-waves 220, 222 shown in FIG. 2, the T-wave amplitude 244 may vary between the T-waves 220, 222.

In order to treat tachycardia, or an accelerated heart rate, the IMD 100 may monitor a ventricular heart rate $V_{RATE}$ of the heart 102. In one embodiment, the IMD 100 monitors the ventricular heart rate $V_{RATE}$ by determining how frequently QRS complexes occur. The IMD 100 may determine how frequently the QRS complexes occur by measuring how frequently cardiac signal waveforms exceed a predetermined threshold. For example, the IMD 100 may calculate how frequently cardiac signals exceed a detection threshold 246. The detection threshold 246 may be programmably stored in a memory. Cardiac signals that exceed the detection threshold 246 are identified as candidate waveforms. The candidate waveforms may be used by the IMD 100 to determine the ventricular heart rate $V_{RATE}$. For example, the IMD 100 may calculate the frequency at which the candidate waveforms occur to be the ventricular heart rate $V_{RATE}$.

If the ventricular heart rate $V_{RATE}$ exceeds a predetermined threshold, the IMD 100 may then determine that the heart 102 is experiencing tachycardia. The IMD 100 may then apply stimulation pulses to the heart 102 to treat the tachycardia. As shown in FIG. 2, only the amplitude 242 of the QRS complexes 228, 230 exceeds the detection threshold 246. As a result, the IMD 100 may treat only the QRS complexes 228, 230 as candidate waveforms and base the ventricular heart rate $V_{RATE}$ on the frequency at which the QRS complexes 228, 230 occur. If the frequency at which the QRS complexes 228, 230 occurs does exceed a predetermined threshold, then the heart 102 may be experiencing tachycardia. But, cardiac signal waveforms other than the QRS complexes 228, 230 may exceed the detection threshold 246. By way of example only, a patient's T-waves 220, 222 may increase in size to larger T-waves 248, 250 due to medication taken by a patient, cardiac disease of the heart 102, and the like. When the larger T-waves 248, 250 exceed the detection threshold 246, the IMD 100 may identify the larger T-waves 248, 250 as candidate waveforms. Alternatively, the detection threshold may be set low enough such that both of the QRS amplitude 242 and the T-wave amplitude 244 exceed the detection threshold. For example, a patient's normal T-waves 220, 222 may be larger than the detection threshold 244. In either case, the IMD 100 may count both the QRS complex and the T-wave in each cardiac cycle 200, 202 as candidate waveforms.

If the IMD 100 counts both the QRS complexes 228, 230 and the T-waves 248, 250 as candidate waveforms and bases the calculation of the ventricular heart rate $V_{RATE}$ on the frequency of these candidate waveforms, then the IMD 100 may incorrectly calculate the ventricular heart rate $V_{RATE}$. For example, the IMD 100 may calculate the ventricular heart rate $V_{RATE}$ as exceeding a predetermined threshold and then apply stimulation pulses to the heart 102 in response thereto. If a ventricular heart rate $V_{RATE}$ that is based on the frequency of QRS complexes 228, 230 alone would not exceed the predetermined threshold, but a ventricular heart rate $V_{RATE}$ that is based on the frequency of the QRS complexes 228, 230 and the T-waves 248, 250 would exceed the predetermined threshold, the IMD 100 may unnecessarily apply stimulation pulses when the ventricular heart rate $V_{RATE}$ is based on the frequency of both the QRS complexes 228, 230 and the T-waves 248, 250.

In order to avoid unnecessary application of stimulation pulses to the heart 102, the IMD 100 may avoid counting both the QRS complex and the T-wave as candidate waveforms. To avoid double-counting the number of QRS complexes in each cardiac cycle 200, 202, the IMD 100 may discriminate between the different waveforms in the cardiac cycles 200, 202. For example, the IMD 100 may discern between the QRS complexes and the T-waves to avoid counting the T-waves as additional QRS complexes.

Figure 3:
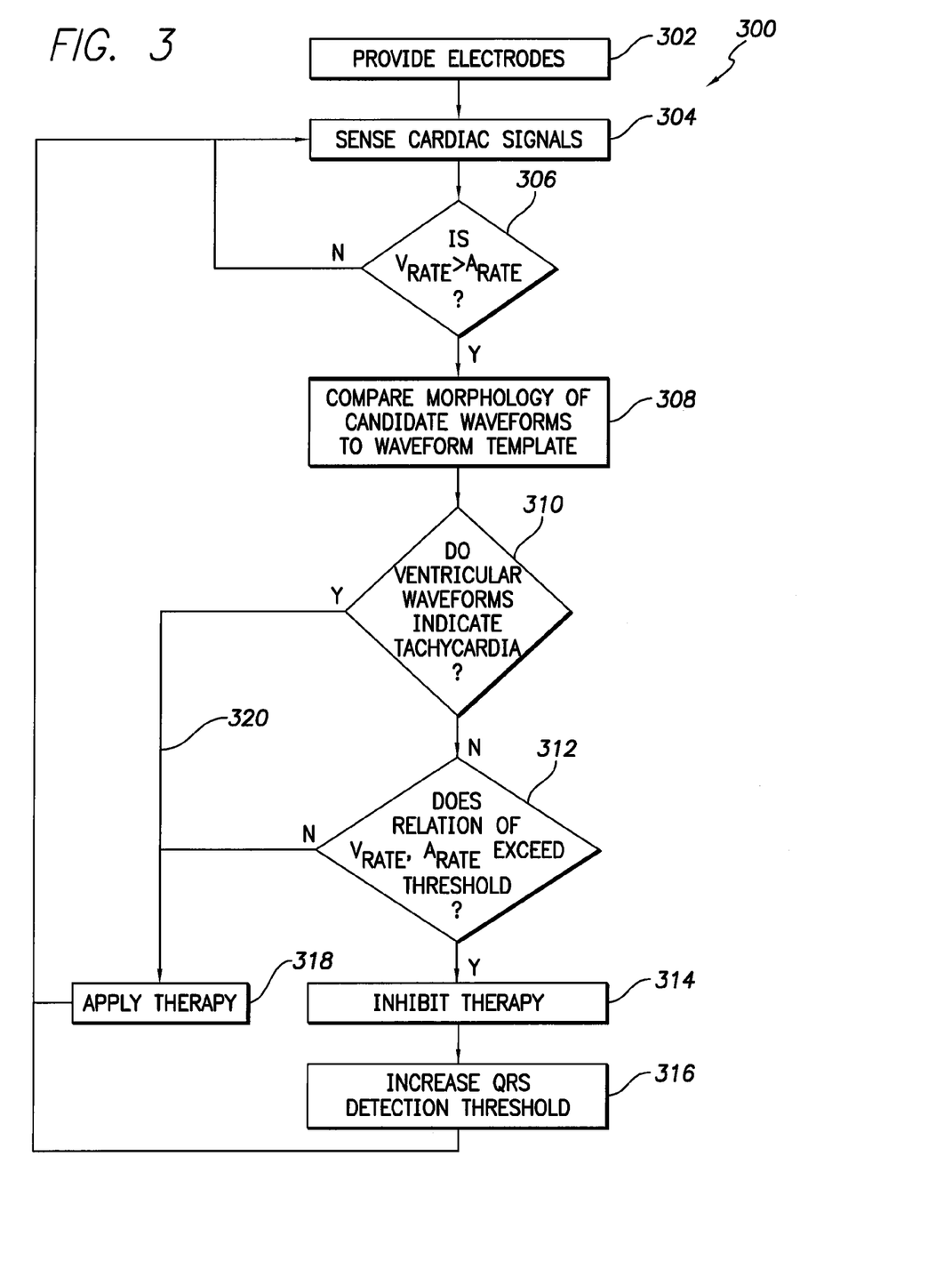
FIG. 3 illustrates a process for discriminating between cardiac signal waveforms in accordance with one embodiment.

FIG. 3 illustrates a process 300 for discriminating between cardiac signal waveforms in accordance with one embodiment. At block 302, one or more electrodes are positioned proximate the heart 102. At block 304, cardiac signals are sensed by the electrodes, such as over a predetermined time window (e.g., 15 seconds). Alternatively, the cardiac signals may be sensed for a time window that is defined by a predetermined number of heart beats. The ventricular heart rate $V_{RATE}$ and an atrial heart rate $A_{RATE}$ may be determined at block 304 based on the sensed cardiac signals. As described above, the ventricular heart rate $V_{RATE}$ may be calculated by determining the frequency at which candidate waveforms occur over a predetermined time window. The atrial heart rate $A_{RATE}$ may be calculated by counting the number of atrial waveforms that occur during the predetermined time window. The atrial waveforms that are counted may include the P-waves 204, 206 (shown in FIG. 2).

At block 306, the ventricular and atrial heart rates $V_{RATE}$, $A_{RATE}$ are analyzed to determine if the ventricular heart rate $V_{RATE}$ exceeds the atrial heart rate $A_{RATE}$. If the candidate waveforms upon which the ventricular heart rate $V_{RATE}$ is based include both a QRS complex and a T-wave in each cardiac cycle 200, 202 and the atrial heart rate $A_{RATE}$ is based on the counting of a single P-wave in each cardiac cycle 200, 202, then the ventricular heart rate $V_{RATE}$ may be at least twice as great as the atrial heart rate $A_{RATE}$. If the ventricular heart rate $V_{RATE}$ exceeds the atrial heart rate $A_{RATE}$, the flow of the process 300 continues to block 308. If the ventricular heart rate $V_{RATE}$ is based on counting only a QRS complex in each cardiac cycle 200, 202 and the atrial heart rate $A_{RATE}$ is based on counting only a P-wave in each cardiac cycle 200, 202, then the ventricular heart rate $V_{RATE}$ may be approximately the same as the atrial heart rate $A_{RATE}$. When the ventricular heart rate $V_{RATE}$ does not exceed the atrial heart rate $A_{RATE}$, the flow of the process 300 returns to block 304 where additional cardiac signals are sensed by the electrodes.

At block 308, the morphologies of the candidate waveforms that were counted at block 306 are compared to one or more predetermined waveform templates to determine whether the candidate waveforms represent ventricular waveforms of interest. A ventricular waveform of interest may be a QRS complex or a T-wave, for example. In one embodiment, each of the candidate waveforms is compared to at least one waveform template that represents a QRS complex. The candidate waveforms are compared to the QRS waveform template to determine which of the candidate waveforms is a QRS complex. Optionally, the candidate waveforms may be compared to a waveform template that represents a T-wave. The candidate waveforms may then be compared to one or both of the QRS and T-wave waveform templates to determine which of the candidate waveforms is a QRS complex and which of the candidate waveforms is a T-wave.

The candidate waveforms are compared to the waveform templates to determine morphology indicators. A morphology indicator is a quantifiable degree to which a candidate waveform corresponds to or matches a waveform template. For example, a morphology indicator may represent the correlation between a candidate waveform and a waveform template. The morphology indicator may indicate the strength and direction of relationship between the candidate waveform and the waveform template. Each of first and second candidate waveforms may be compared to a waveform template to determine first and second morphology indicators, respectively. As described below, a smaller morphology indicator may represent a closer match or better correlation between a candidate waveform and a waveform template than a larger morphology indicator. For example, if the first morphology indicator is smaller than the second morphology indicator, then the first morphology indicator represents that the first candidate waveform is more closely correlated with the waveform template than the second candidate waveform. As a result, the first candidate waveform may be identified as the waveform represented by the waveform template while the second candidate waveform is not identified as the waveform represented by the waveform template or is identified as another waveform. An example of how morphology indicators may be calculated is described below in connection with FIG. 4.

Figure 4:
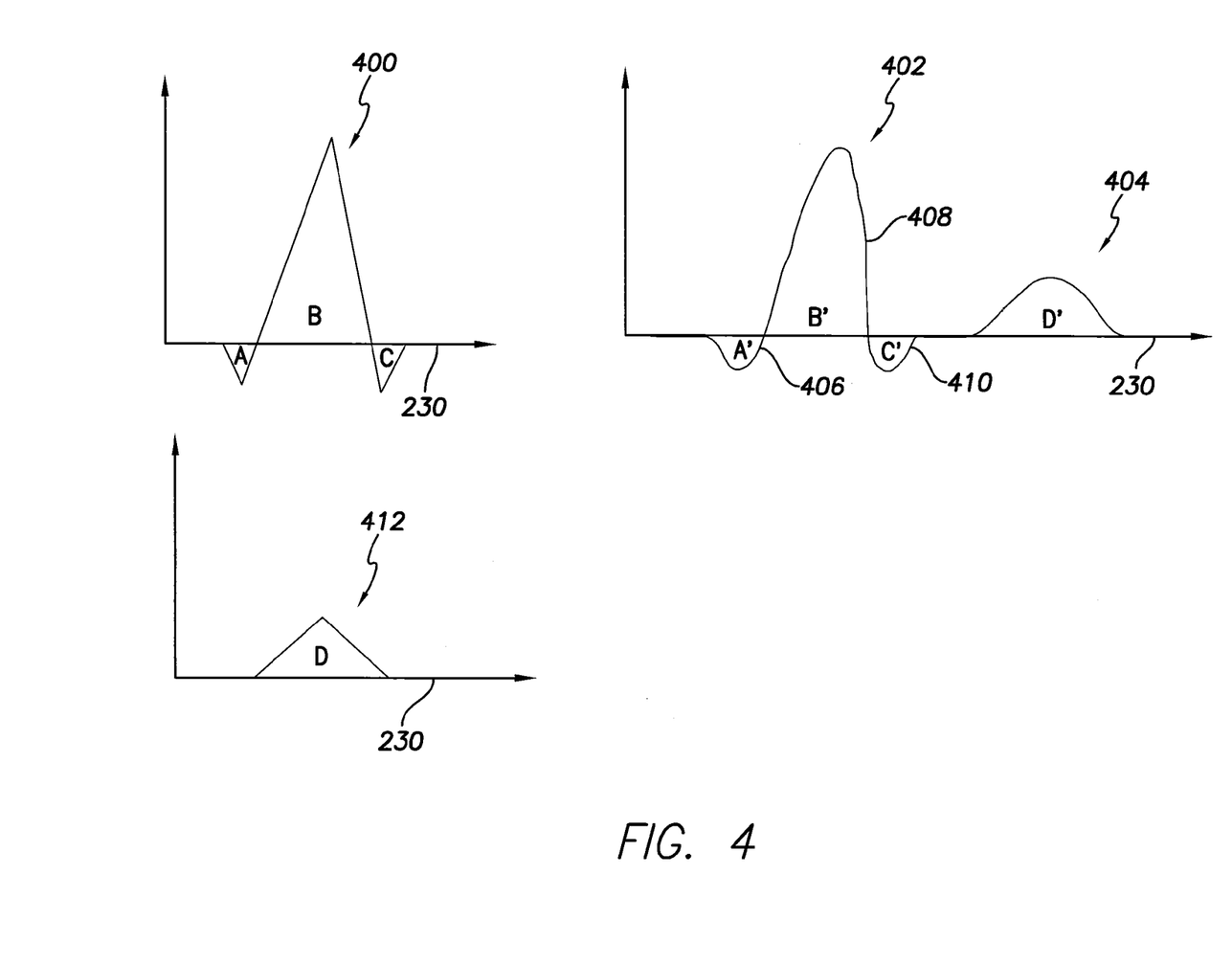
FIG. 4 illustrates an example of first and second waveform templates according to one embodiment.

FIG. 4 illustrates an example of how first and second candidate waveforms 402, 404 may be compared to first and second predetermined waveform templates 400, 412 to determine morphology indicators. The first waveform template 400 is shaped similar to and represents a QRS complex and the second waveform template 412 is shaped similar to and represents a T-wave. For example, the first waveform template 400 may include three fragments labeled A, B and C that approximate the general shapes of the Q-wave, the R-wave and the S-wave of a QRS complex. The second waveform template 412 includes a single fragment labeled D that approximates the general shape of the T-wave. The waveform templates 400, 412 are provided as examples and one or more different waveform templates may be used. For example, the templates may be square waves, semi-circular waves, etc., and include more or fewer than three blocks such as A, B and C.

Each of the first and second candidate waveforms 402, 404 may be compared to the first and second waveform templates 400, 412 to calculate first and second morphology indicators, respectively. In one embodiment, the first and second candidate waveforms 402, 404 may be compared to the first and second waveform templates 400, 412 to calculate third and fourth morphology indicators, or an additional first morphology indicator and an additional second morphology indicator. If the first morphology indicator is larger than the second morphology indicator, then the first morphology indicator may represent that the first candidate waveform 402 is a QRS complex represented by the first waveform template. If the fourth morphology indicator, or the additional second morphology indicator, is greater than the third morphology indicator, or the additional first morphology indicator, then the fourth morphology indicator may represent that the second candidate waveform 412 is a T-wave represented by the second waveform template.

Returning to FIG. 3, block 308, the various morphology indicators may be calculated by comparing the areas of various fragments of the candidate waveforms 402, 404 with the areas of the fragments A, B, C, and D of the waveform templates 400, 412. The areas of the fragments A, B, C, and D may be calculated and stored in a memory. The first candidate waveform 402 may be analyzed by separating the waveform 402 into first through third fragments A', B' and C' and calculating the area of each of the fragments A', B', C'. The first fragment A' may be identified by the IMD 100 by determining the initial portion of the waveform 402 that extends below the baseline 230. The second fragment B' may be identified by the IMD 100 as the portion of the waveform 402 that follows the first fragment A' and that extends above the baseline 230. The third fragment C' may be identified by the IMD 100 as the final portion of the waveform 402 that returns below the baseline 230 and that follows the second fragment B'. The second candidate waveform 404 may be analyzed by identifying and calculating an area of a fourth fragment D'. The fourth fragment D' represents the portion of the second candidate waveform 404 that extends above the baseline 230 and that is not preceded or followed by waveform portions that extend below the baseline 230. The areas of the fragments A', B', C' and D' may be calculated using various methods. For example, mathematical curves or models may be fit to each of the fragments A', B', C' and D'. The areas of the fragments A', B', C' and D' may then be calculated by integrating the curves with respect to the baseline 230.

The first morphology indicator may be determined by calculating the absolute value of the differences between the areas of the fragments A, B and C of the first waveform template 400, on one hand, and the areas of the fragments A', B' and C' of the first candidate waveform 402, on the other hand. For example, the first morphology indicator may be calculated using the following relationship:

$$M=ABS(A-A')+ABS(B-B')+ABS(C-C') \qquad \text{(Eqn. 1)}$$

where M is the morphology indicator, ABS(A–A') is the absolute value of the difference between the areas of the fragments A and A', ABS(B–B') is the absolute value of the difference between the areas of the fragments B and B', and ABS(C–C') is the absolute value of the difference between the areas of the fragments C and C'.

The second morphology indicator may be determined by calculating the area of the fragment D' of the second candidate waveform 404. and then comparing the area to the areas of the fragments A', B', C' of the first waveform template 400 using Equation #1 shown above. Because the fragment D' of the second candidate waveform 404 extends above the baseline 230, the area D' is compared to the area of the fragment B of the first waveform template 400. No substantial part of the second candidate waveform 404 extends below the baseline 230 before or after the fragment D'. Hence, when the second candidate waveform 404 is compared to the areas of the fragments A and C of the first waveform template 400, the absolute values of the difference between the areas of fragments A and A' and between the areas of fragments C and C' are relatively large values. Using the Equation #1 above, the second morphology indicator between the first waveform template 400 and the second candidate waveform 404 therefore effectively is determined as follows:

$$M=A+ABS(B-D)+C \qquad \text{(Eqn. 2)}$$

The sum total of (1) the areas of the fragments A and C of the first waveform template 400 and (2) the difference between the area of the fragment B of the first waveform template 400 and the area of the fragment D' of the second candidate waveform 404 may be relatively large. Thus, the second morphology indicator that is associated with the second candidate waveform 404 is determined to be greater than the first morphology indicator that is associated with the first candidate waveform 402. Consequently, the first candidate waveform 402 is determined to more closely match the first waveform template 400.

Next, the first candidate waveform 402 may be compared with the second waveform template 412 to determine the third morphology indicator, or the additional first morphology indicator. The areas of the fragments A', B' and C' of the first candidate waveform 402 are compared to the area of the fragment D of the second waveform template 412 using the following relationship:

$$M=ABS(D-B')+\Delta \qquad \text{(Eqn. 3)}$$

where M is the third morphology indicator, ABS(D–B') represents the absolute value of the difference between the area of the fragment D of the second waveform template 412 and the area of the fragment B' of the first candidate waveform 402, and $\Delta$ represents the sum total of the areas of additional fragments of the first candidate waveform 402 that extend above and below the baseline 230 or that have no corresponding counterpart fragment in the second waveform template 412. For example, $\Delta$ represents the total area of the fragments A' and C' of the first candidate waveform 402.

The second candidate waveform 404 is then compared to the second waveform template 412 to determine the fourth morphology indicator, or the additional second morphology indicator. The fourth morphology indicator is calculated using Equation #3 in one embodiment. For example, the fourth morphology indicator may represent the absolute difference between the areas of the fragment D of the second waveform template 412 and the area of the fragment D' of the second candidate waveform 404. The second candidate waveform 404 does not include any additional areas below or above the baseline 230, and thus the value of $\Delta$ for the second candidate waveform 404 approaches zero. The morphology indicators may be stored in a memory for later analysis by the IMD 100.

Optionally, at block 308, the morphology indicators may be expressed as percentages of correlation or match between the candidate waveforms 402, 404 and the waveform templates 400, 412. The percentage of correlation may range in value between zero and 100 percent, with zero percent indicating a low degree of match or correlation between a candidate waveform and a waveform template. A percentage of correlation of 100 percent indicates a high degree of match or correlation between a waveform and a waveform template.

The percentage of correlation between the candidate waveforms 402, 404 and the waveform templates 400, 412 may be compared to upper and lower predetermined thresholds to characterize the candidate waveform 402, 404 as being a waveform of interest represented by a corresponding one of the waveform templates 400, 412. For example, the first candidate waveform 402 may be compared to (1) the first waveform template 400 to calculate a first percentage of correlation of 93% and (2) the second waveform template 412 to calculate a second percentage of correlation of 4%. If the upper threshold is 90% and the lower threshold is 10%, then the first candidate waveform 402 may be identified at 308 to be a QRS complex represented by the first waveform template 400. Moreover, the first candidate waveform 402 may be identified at 308 not to be a T-wave represented by the second waveform template 412. The percentages of correlation for the candidate waveforms 402, 404 and the upper and lower thresholds may be stored in a memory.

Continuing with FIG. 3, block 310, the morphology indicators or the percentages of correlation are examined to determine if the ventricular heart rate $V_{RATE}$ is based on the counting of QRS complexes or is based on the counting of both QRS complexes and T-waves. The morphology indicators or percentages of correlation of the candidate waveforms may be analyzed to determine if a pattern of high and low matches appears. For example, Table 1 below represents the percentages of correlation between several candidate waveforms, on one hand, and first and second waveform templates, on the other hand. The first row in Table #1 includes a numbered series of candidate waveforms that were sensed during the predetermined time window at block 306 to determine the ventricular heart rate $V_{RATE}$. The second and third rows in Table #1 include the percentages of correlation between each of the candidate waveforms and the first and second waveform templates. The percentages of correlation may be obtained from a memory.

TABLE #1

|  | Ventricular waveform number: | | | | | |
| --- | --- | --- | --- | --- | --- | --- |
|  | 1 | 2 | 3 | 4 | 5 | 6 |
| Match with first waveform template: | 92% | 95% | 91% | 98% | 93% | 92% |
| Match with second waveform template | 5% | 3% | 7% | 1% | 6% | 8% |

As shown in Table #1, the candidate waveforms numbered 1 through 6 demonstrate a continuous pattern of a high percentage of correlation with the first waveform template 400 and a continuous pattern of a low percentage of correlation with the second waveform template 412. Consequently, the candidate waveforms counted at block 306 are identified as QRS complexes at block 310. Additionally, the ventricular heart rate $V_{RATE}$ that was calculated at block 306 is determined to be based on the frequency at which the QRS complexes occurred. The process 300 determines at block 310 that the ventricular heart rate $V_{RATE}$ is based on the frequency of QRS complexes and is not based on the incorrect counting of T-waves. As a result, the flow of the process 300 continues to block 318

Table #2 below illustrates the percentages of correlation between several candidate waveforms, on one hand, and first and second waveform templates, on the other hand.

TABLE #2

|  | Ventricular waveform number: | | | | | |
| --- | --- | --- | --- | --- | --- | --- |
|  | 1 | 2 | 3 | 4 | 5 | 6 |
| Match with first waveform template: | 94% | 4% | 95% | 2% | 98% | 3% |
| Match with second waveform template | 3% | 93% | 2% | 92% | 1% | 97% |

In contrast to the continuous patterns shown in Table #1, Table #2 illustrates alternating patterns of high and low percentages of correlation between the candidate waveforms and the waveform templates 400, 412. The odd-numbered candidate waveforms are associated with relatively high percentages of correlation with the first waveform template 400 and relatively low percentages of correlation with the second waveform template 412. The even-numbered candidate waveforms are associated with relatively low percentages of correlation with the first waveform template 400 and relatively high percentages of correlation with the second waveform template 412. Therefore, the odd-numbered candidate waveforms are identified as QRS complexes and the even-numbered candidate waveforms are identified as T-waves. As a result, at 310, the ventricular heart rate $V_{RATE}$ that was calculated at 306 is determined to be based on the incorrect counting of T-waves as additional QRS complexes. Accordingly, the candidate waveforms counted at 306 are not declared to indicate that the heart 102 is demonstrating tachycardia. While the examples described above in connection with Tables #1 and 2 compare the candidate waveforms to both the first and second waveform templates 400, 412, alternatively the ventricular waveforms may only be compared to one of the two waveform templates 400, 412.

If, at block 310, the process 300 determines that the ventricular heart rate $V_{RATE}$ is based on counting QRS complexes and is not based on counting both QRS complexes and T-waves, the flow of the process 300 moves to 318 along path 320. At 318, a therapy to treat the tachycardia is applied to the heart 102. For example, the process 300 may permit initiation of a therapy that applies stimulation pulses to the heart 102 by the IMD 100. After the therapy is applied, the flow of the process 300 returns to 304, where additional cardiac signals are sensed by the electrodes.

Alternatively, if, at block 310, the process 300 determines that the ventricular heart rate $V_{RATE}$ is based on counting QRS complexes and T-waves, the flow of the process 300 moves to block 312. At block 312, the ventricular heart rate $V_{RATE}$ and the atrial heart rate $A_{RATE}$ are compared to determine if the ventricular heart rate $V_{RATE}$ exceeds the atrial heart rate $A_{RATE}$ by a sufficient amount. For example, a relation of the ventricular heart rate $V_{RATE}$ and the atrial heart rate $A_{RATE}$ may be compared to a predetermined ratio as a safety check on the analysis performed at block 310. As shown in FIG. 2, there are two ventricular waveforms (for example, a QRS complex 228 and a T-wave 220 or 248) and one atrial waveform (for example, a P-wave 204) in each cardiac cycle 200. If both QRS complexes and T-waves are used to calculate the ventricular heart rate $V_{RATE}$ and the P-wave is used to calculate the atrial heart rate $A_{RATE}$ at 304, then the ventricular heart rate $V_{RATE}$ may be at least twice as large as the atrial heart rate $A_{RATE}$. Conversely, if QRS complexes but not T-waves are used to calculate the ventricular heart rate $V_{RATE}$ and the P-wave is used to calculate the atrial heart rate $A_{RATE}$, then the ventricular heart rate $V_{RATE}$ may not be at least twice as large as the atrial heart rate $A_{RATE}$. If the ventricular heart rate $V_{RATE}$ exceeds the atrial heart rate $A_{RATE}$ by the predetermined amount or ratio, then the flow of the process 300 flows from block 312 to block 314. If the ventricular heart rate $V_{RATE}$ does not exceed the atrial heart rate $A_{RATE}$ by the predetermined amount, then the flow of the process 300 flows from block 312 to block 318, where a therapy is applied to the heart 102, as described above.

At block 314, the therapy that would be applied to the heart 102 in order to treat tachycardia is inhibited. For example, the IMD 100 may refrain from applying one or more stimulation pulses to the heart 102 to treat tachycardia. In doing so, the process 300 may discriminate between QRS complexes 228, 230 (shown in FIG. 2) and T-waves 248, 250 (shown in FIG. 2) to avoid incorrectly calculating an accelerated ventricular heart rate $V_{RATE}$ and erroneously applying stimulation pulses to the heart 102 to treat the ventricular heart rate $V_{RATE}$.

At block 316, the detection threshold 246 (shown in FIG. 2) may be increased. For example, the detection threshold 246 may be increased by a fixed, predetermined amount. Alternatively, the detection threshold 246 may be increased by a predetermined percentage of the current detection threshold 246. The detection threshold 246 may be increased in order to reduce the possibility that the IMD 100 will continue to incorrectly identify T-waves 248, 250 (shown in FIG. 2) as QRS complexes 228, 230 (shown in FIG. 2). For example, as shown in FIG. 2, if the detection threshold 246 is increased to a value that is greater than the amplitude of the T-waves 248, 250, then the T-waves 248, 250 may no longer be incorrectly identified by the IMD 100 as being QRS complexes 228, 230. The flow of the process 300 may then return to 304 where additional cardiac signals are sensed by the electrodes.

In an alternative embodiment, one or more of the operations of the process 300 described above are omitted. For example, the operations described at block 312 may be omitted from the process 300. In such an embodiment, once a determination is made at block 310 as to whether the ventricular waveforms do or do not indicate tachycardia, the flow of the process 300 continues to block 314 or block 318 where a responsive therapy is accordingly inhibited or applied. In another example, the operations described at block 316 may be omitted. For example, the detection threshold 246 may not be increased after a pacing therapy is inhibited at block 314.

Figure 5:
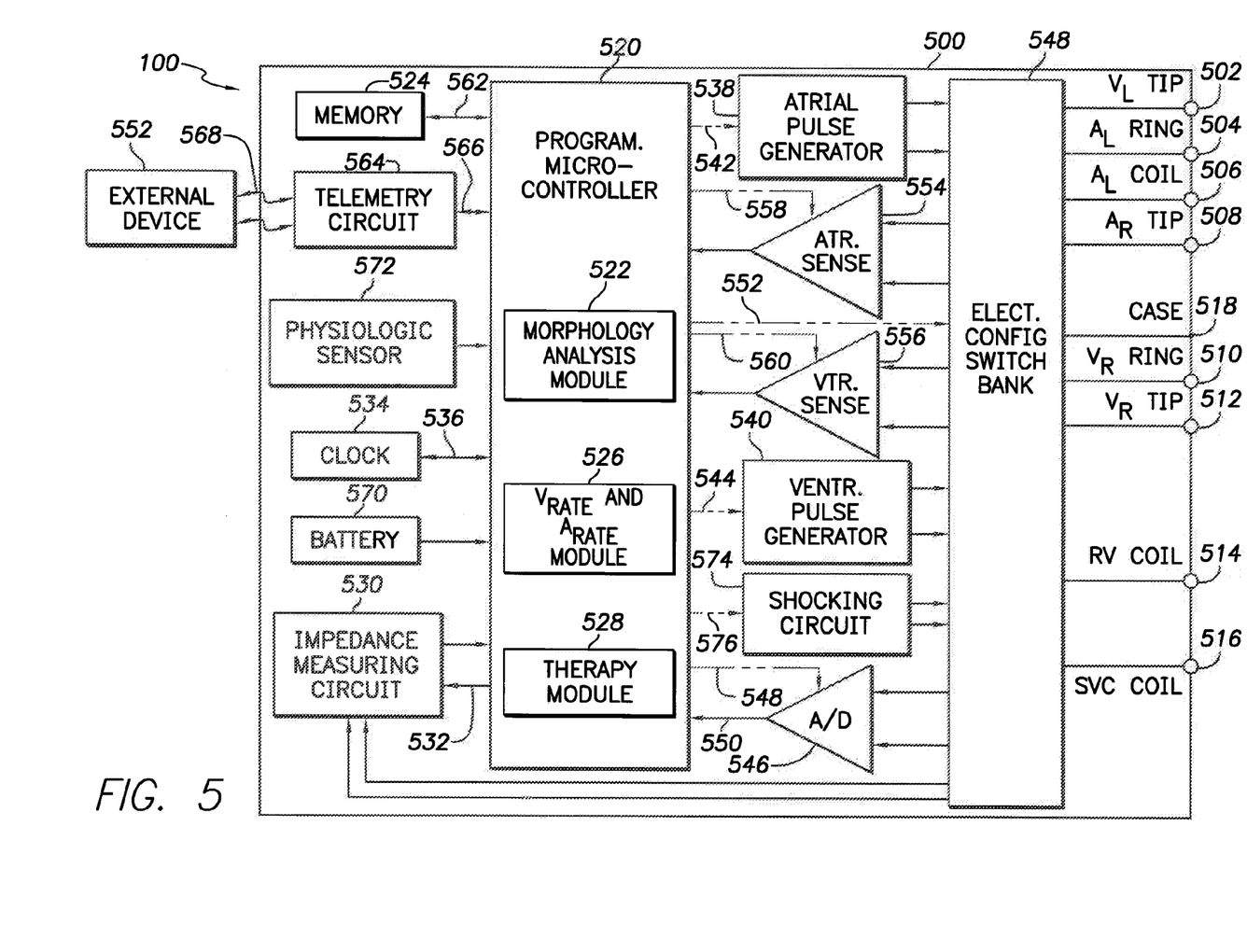
FIG. 5 illustrates a block diagram of exemplary internal components of the implantable medical device shown in FIG. 1.

FIG. 5 illustrates a block diagram of exemplary internal components of the IMD 100. The IMD 100 includes the housing 500 that includes a left ventricle tip input terminal ($V_L$ TIP) 502, a left atrial ring input terminal ($A_L$ RING) 504, a left atrial coil input terminal ($A_L$ COIL) 506, a right atrial tip input terminal ($A_R$ TIP) 508, a right ventricular ring input terminal ($V_R$ RING) 510, a right ventricular tip input terminal ($V_R$ TIP) 512, an RV coil input terminal 514 and an SVC coil input terminal 516. A case input terminal 518 may be coupled with the housing 500 of the IMD 100. The input terminals 502-518 may be electrically coupled with the electrodes 120-138 (shown in FIG. 1).

The IMD 100 includes a programmable microcontroller 520, which controls the operation of the IMD 100 based on acquired cardiac signals. The microcontroller 520 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. Among other things, the microcontroller 520 receives, processes, and manages storage of digitized data from the various electrodes 120-138 (shown in FIG. 1). The microcontroller 520 may include one or more modules and processors configured to perform one or more of the operations described above in connection with the process 300. A morphology analysis module 522 compares ventricular waveforms sensed by ventricular sense circuit 556 with one or more of the waveform templates 400, 412 (shown in FIG. 4), as described above. The morphology analysis module 522 may calculate the percentages of match or mismatch between the ventricular waveforms and the waveform templates 400, 412. The morphology analysis module 522 may obtain the waveform templates 400, 412 from a memory 524 of the IMD 100. Previously obtained cardiac signal waveforms may be obtained by the morphology analysis module 522 also may be obtained from the memory 524 for comparing to the waveform templates 400, 412.

A ventricular and atrial rate calculation module 526 calculates the ventricular heart rate $V_{RATE}$ and the atrial heart rate $A_{RATE}$ based on the cardiac signals sensed by atrial sense circuit 554 and ventricular sense circuit 556. The rate calculation module 526 may compare the ventricular and atrial rates as described above in connection with the process 300.

A therapy module 528 determines whether to permit or inhibit the application of one or more stimulation pulses to the heart 102 to treat tachycardia based on the analysis described above in connection with the process 300. For example, the therapy module 528 may examine the percentages or match or mismatches between the ventricular waveforms of interest and the waveform templates 400, 412 (shown in FIG. 4) to determine whether patterns in the percentages of match appear, as described above. The therapy module 528 may direct an excitation source to deliver or not deliver the stimulation pulses to the heart 102. The pulse generators 538, 540 are controlled via appropriate control signals 542, 544 to trigger or inhibit the stimulation pulses. In the case where IMD 100 is permitted by the therapy module 528 to apply stimulation pulses to the heart 102, the IMD 100 applies an appropriate electrical shock therapy to the heart. To this end, the microcontroller 520 further controls a shocking circuit 574 by way of a control signal 576. The shocking circuit 668 generates shocking pulses of low (up to 0.5 joules), moderate (0.5-10 joules) or high energy (11 to 40 joules). Such stimulation pulses are applied to the heart 102 of the patient through one or more of the electrodes 120-138.

The cardiac signals sensed by the electrodes 120-138 are applied to the inputs of the analog-to-digital (A/D) data acquisition system 546. For example, the cardiac signals indicative of atrial and ventricular waveforms may be sensed by the electrodes 120-138 and communicated to the data acquisition system 546. The cardiac signals are communicated through the input terminals 502-516 to an electronically configured switch bank, or switch, 548 before being received by the data acquisition system 546. The data acquisition system 546 converts the raw analog data of the signals obtained by the electrodes 120-138 into digital signals 550 and communicates the signals 550 to the microcontroller 520. A control signal 548 from the microcontroller 520 determines when the data acquisition system 546 acquires signals, stores the signals 550 in the memory 524, or transmits data to an external device 552.

The switch 548 includes a plurality of switches for connecting the desired electrodes 120-138 (shown in FIG. 1) and input terminals 502-518 to the appropriate circuits. The switch 548 closes and opens switches to provide electrically conductive paths between the circuitry of the IMD 100 and the input terminals 502-518 in response to a control signal 552. An atrial sensing circuit 554 and a ventricular sensing circuit 556 may be selectively coupled to the leads 108-112 (shown in FIG. 1) of the IMD 100 through the switch 548 for detecting the presence of cardiac activity in the chambers of the heart 106 (shown in FIG. 1). The sensing circuits 554, 556 sense the cardiac signals that are analyzed by the microcontroller 520. Control signals 558, 560 from the microcontroller 520 control the sensing threshold, and other operation characteristics, of the sensing circuits 554, 556. An impedance measuring circuit 530 is enabled by the microcontroller 520 via a control signal 532. The impedance measuring circuit 530 may be electrically coupled to the switch 548 so that an impedance vector between any desired pairs of electrodes 120-138 may be obtained. The IMD 100 additionally includes a battery 570 that provides operating power to the circuits shown within the housing 500, including the microcontroller 520. The IMD 100 includes a physiologic sensor 572 that may be used to adjust pacing stimulation rate according to the exercise state of the patient.

A clock 534 may measure time relative to the cardiac cycles or cardiac signal waveforms of the heart 102. The clock 534 measures elapsed amounts of time based on start and stop control signals 536 from the microcontroller 520 to determine the ventricular and atrial heart rates. The memory 524 may be embodied in a computer-readable storage medium such as a ROM, RAM, flash memory, or other type of memory. The microcontroller 520 is coupled to the memory 524 by a suitable data/address bus 562. The memory 524 may store programmable operating parameters and thresholds used by the microcontroller 520, as required, in order to customize the operation of IMD 100 to suit the needs of a particular patient. For example, the memory 524 may store data indicative of cardiac signal waveforms, the detection thresholds 246 (shown in FIG. 2), and ventricular and atrial heart rates. The operating parameters of the IMD 100 and thresholds may be non-invasively programmed into the memory 524 through a telemetry circuit 564 in communication with the external device 552, such as a trans-telephonic transceiver or a diagnostic system analyzer. The telemetry circuit 564 is activated by the microcontroller 520 by a control signal 566. The telemetry circuit 564 allows intra-cardiac electrograms, cardiac waveforms of interest, detection thresholds, status information relating to the operation of IMD 100, and the like, to be sent to the external device 552 through an established communication link 568.

Figure 6:
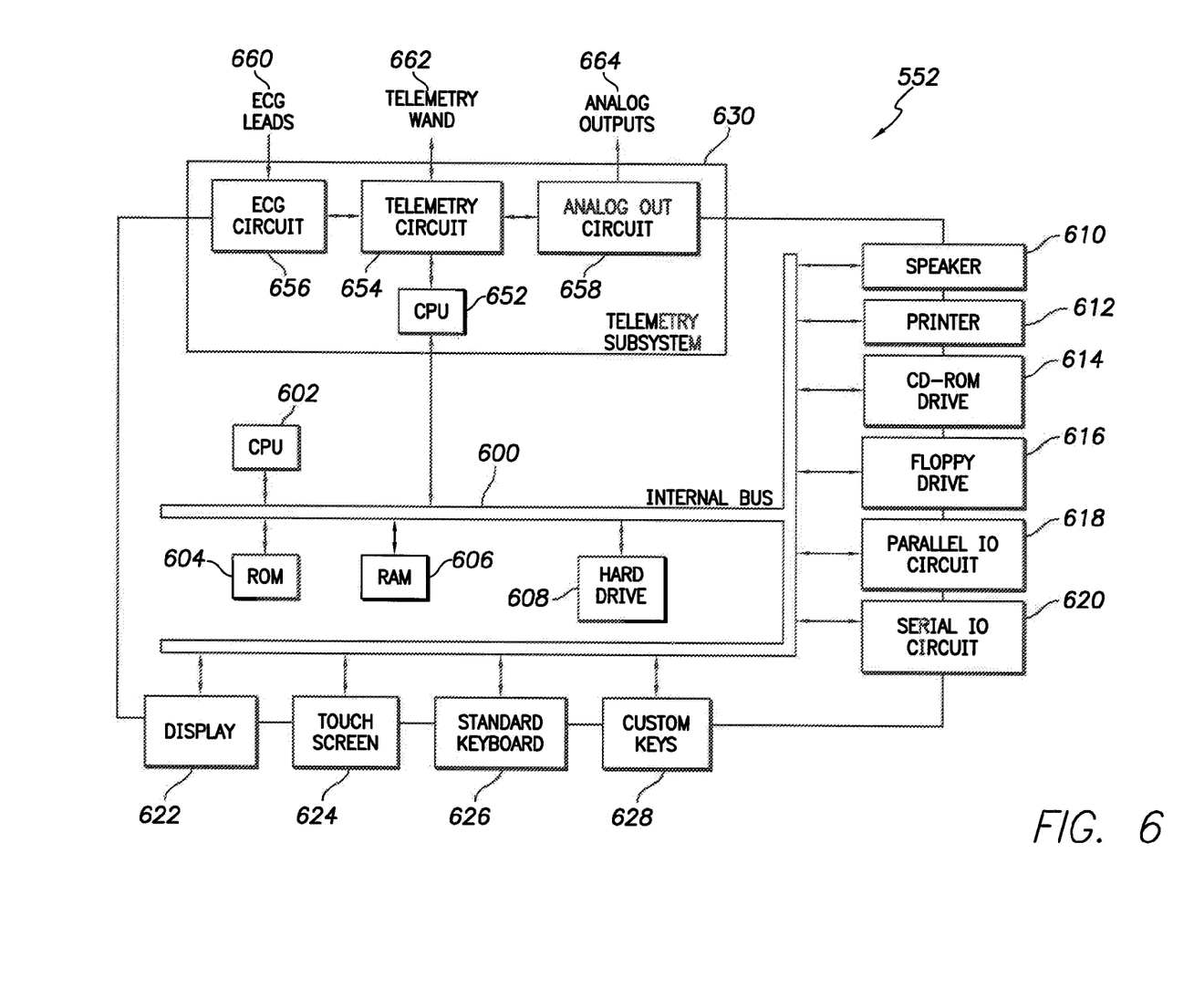
FIG. 6 illustrates a functional block diagram of an external device that is operated to interface with the implantable medical device shown in FIG. 1 according to one embodiment.

FIG. 6 illustrates a functional block diagram of the external device 552, such as a programmer, that is operated to interface with IMD 100. The external device 552 includes an internal bus 600 that connects/interfaces with a central processing unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus 600 is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 552 and with the IMD 100. The CPU 602 may include RAM or ROM memory, logic and timing circuitry, state machine circuitry, and I/O circuitry to interface with the IMD 100. The display 622 and the touch screen 624 display graphic information relating to the IMD 100. The touch screen 624 accepts a user's touch input when selections are made. The keyboard 626 allows the user to enter data to the displayed fields, as well as interface with the telemetry subsystem 630. Furthermore, custom keys 628 turn on/off (e.g., EVVI) the external device 552. The printer 512 prints copies of reports for a physician to review or to be placed in a patient file, and speaker 610 provides an audible warning to the user. The parallel I/O circuit 618 interfaces with a parallel port. The serial I/O circuit 620 interfaces with a serial port. The floppy drive 616 accepts diskettes. Optionally, the floppy drive 616 may include a USB port or other interface capable of communicating with a USB device such as a memory stick. The CD-ROM drive 614 accepts CD ROMs.

The telemetry subsystem 630 includes a central processing unit (CPU) 652 in electrical communication with a telemetry circuit 654, which communicates with both an ECG circuit 656 and an analog out circuit 658. The ECG circuit 656 is connected to ECG leads 660. The telemetry circuit 654 is connected to a telemetry wand 662. The analog out circuit 658 includes communication circuits to communicate with analog outputs 664. The external device 552 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 552 to the IMD 100.

Figure 7:
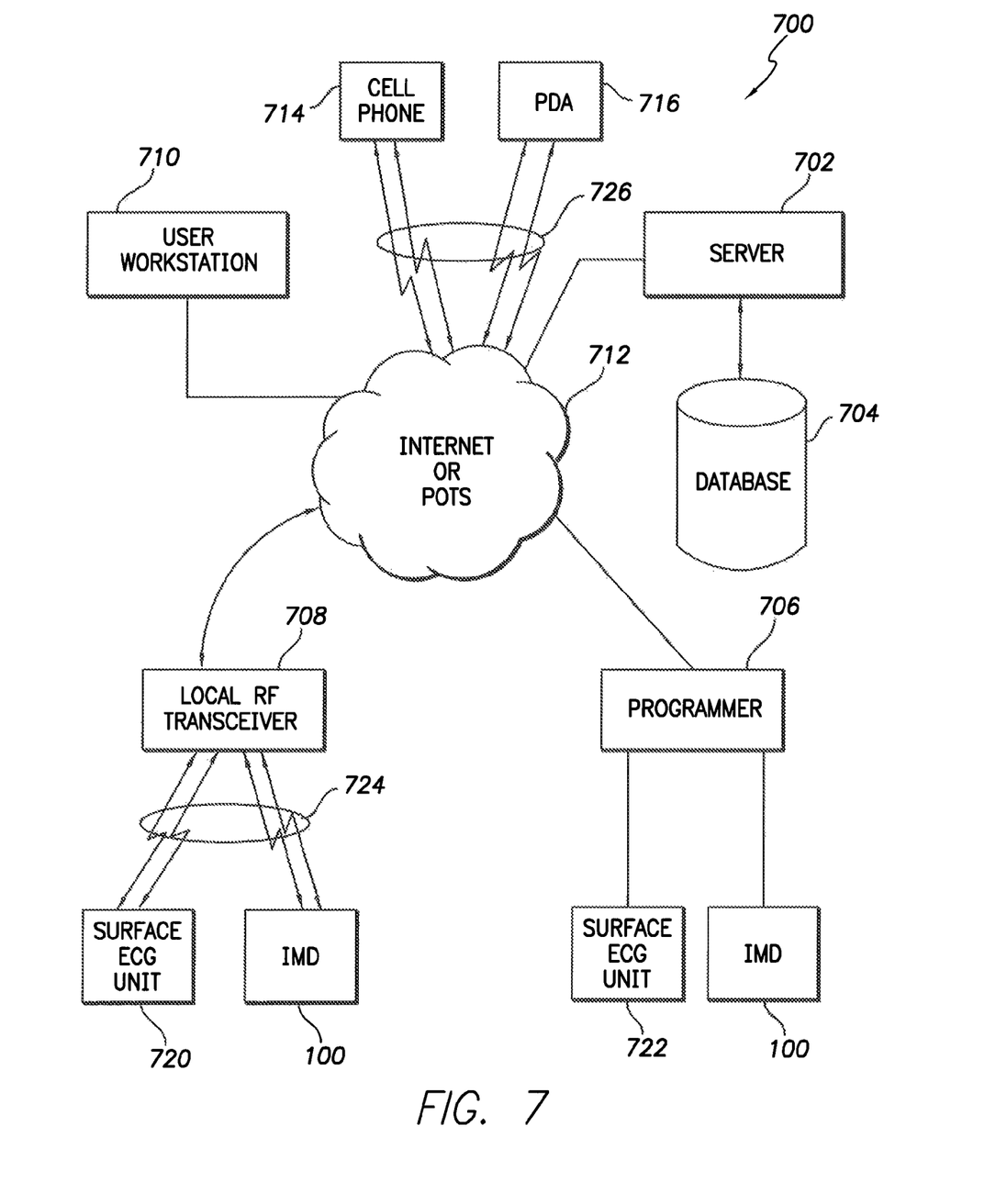
FIG. 7 illustrates a distributed processing system in accordance with one embodiment.

FIG. 7 illustrates a distributed processing system 700 in accordance with one embodiment. The distributed processing system 700 includes a server 702 connected to a database 704, a programmer 706 (e.g., similar to external device 552 (shown in FIG. 5)), a local RF transceiver 708 and a user workstation 710 electrically connected to a communication system 712. The communication system 712 may be the internet, a voice over IP (VoIP) gateway, a local plain old telephone service (POTS) such as a public switched telephone network (PSTN), a cellular phone based network, and the like. Alternatively, the communication system 712 may be a local area network (LAN), a campus area network (CAN), a metropolitan area network (MAN), or a wide area network (WAM). The communication system 712 serves to provide a network that facilitates the transfer/receipt of information such as cardiac signal waveforms, ventricular and atrial heart rates, and detection thresholds 246 (shown in FIG. 2).

The server 702 is a computer system that provides services to other computing systems over a computer network. The server 702 controls the communication of information such as cardiac signal waveforms, ventricular and atrial heart rates, and detection thresholds 246 (shown in FIG. 2). The server 702 interfaces with the communication system 712 to transfer information between the programmer 706, the local RF transceiver 708, the user workstation 710 as well as a cell phone 714 and a personal data assistant (PDA) 716 to the database 704 for storage/retrieval of records of information. On the other hand, the server 702 may upload raw cardiac signals from a surface ECG unit 720, 722 or the IMD 100 via the local RF transceiver 708 or the programmer 706.

The database 704 stores information such as cardiac signal waveforms, ventricular and atrial heart rates, detection thresholds 246 (shown in FIG. 2), and the like, for a single or multiple patients. The information is downloaded into the database 704 via the server 702 or, alternatively, the information is uploaded to the server from the database 704. The programmer 706 is similar to the external device 552 and may reside in a patient's home, a hospital, or a physician's office. The programmer 706 interfaces with the surface ECG unit 722 and the IMD 100. The programmer 706 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 706 to the IMD 100. The programmer 706 is able to acquire cardiac signals from the surface of a person (e.g., ECGs), intra-cardiac electrogram (e.g., IEGM) signals from the IMD 100, and/or cardiac signal waveforms, ventricular and atrial heart rates, and detection thresholds 246 (shown in FIG. 2) from the IMD 100. The programmer 706 interfaces with the communication system 712, either via the internet or via POTS, to upload the information acquired from the surface ECG unit 720 or the IMD 100 to the server 702.

The local RF transceiver 708 interfaces with the communication system 712 to upload one or more of cardiac signal waveforms, ventricular and atrial heart rates, and detection thresholds 246 (shown in FIG. 2) to the server 702. In one embodiment, the surface ECG unit 720 and the IMD 100 have a bi-directional connection 724 with the local RF transceiver 708 via a wireless connection. The local RF transceiver 708 is able to acquire cardiac signals from the surface of a person, intra-cardiac electrogram signals from the IMD 100, and/or cardiac signal waveforms, ventricular and atrial heart rates, and detection thresholds 246 from the IMD 100. On the other hand, the local RF transceiver 708 may download stored cardiac signal waveforms, ventricular and atrial heart rates, and detection thresholds 246, and the like, from the database 704 to the surface ECG unit 720 or the IMD 100.

The user workstation 710 may interface with the communication system 712 via the internet or POTS to download cardiac signal waveforms, ventricular and atrial heart rates, and detection thresholds 246 (shown in FIG. 2) via the server 702 from the database 704. Alternatively, the user workstation 710 may download raw data from the surface ECG units 720, 722 or IMD 100 via either the programmer 706 or the local RF transceiver 708. Once the user workstation 710 has downloaded the cardiac signal waveforms, ventricular and atrial heart rates, or detection thresholds 246, the user workstation 710 may process the information in accordance with one or more of the operations described above in connection with the process 300 (shown in FIG. 3). The user workstation 710 may download the information and notifications to the cell phone 714, the PDA 716, the local RF transceiver 708, the programmer 706, or to the server 702 to be stored on the database 704. For example, the user workstation 710 may communicate data to the cell phone 714 or PDA 716 via a wireless communication link 726.

Figure 8:
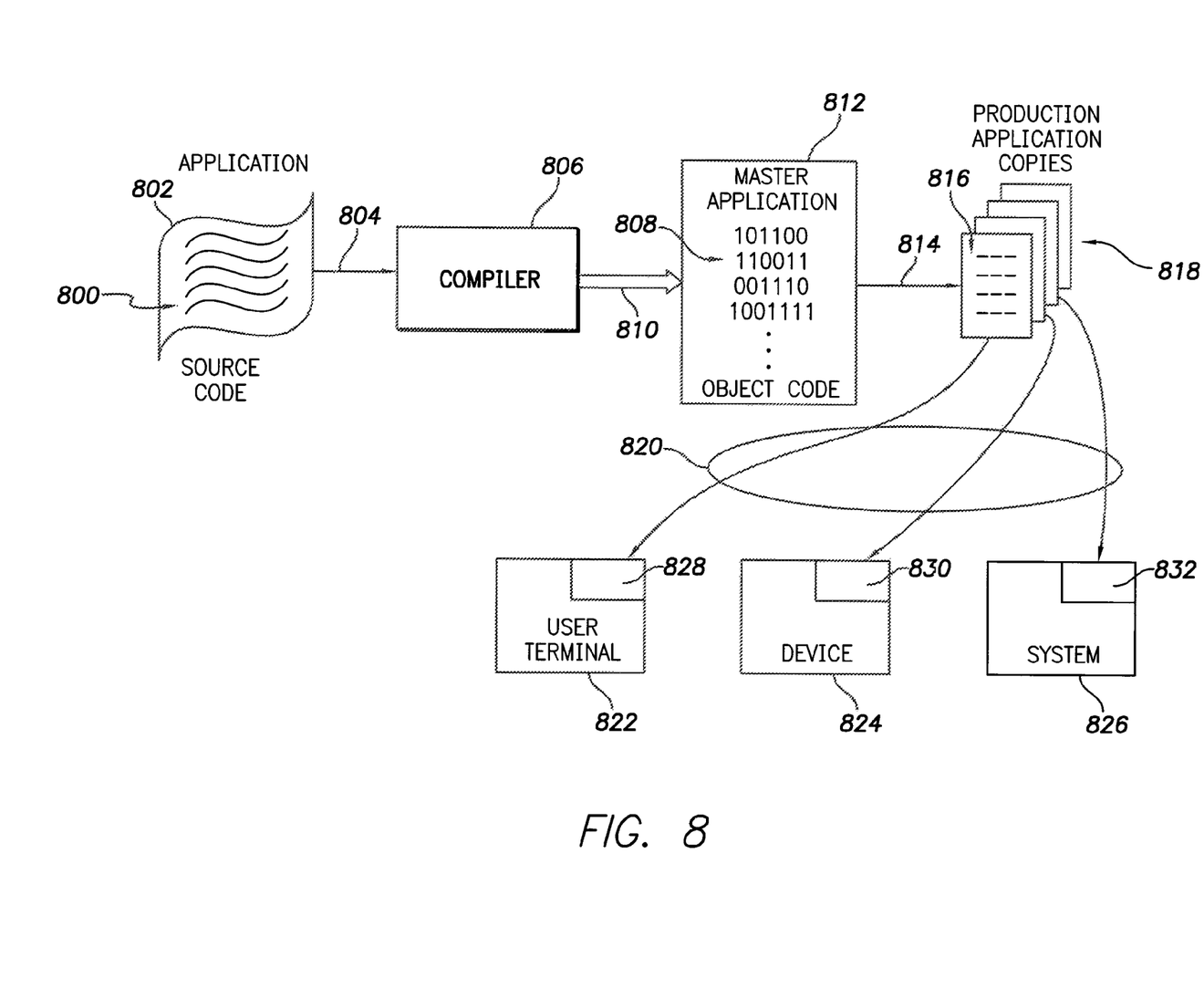
FIG. 8 illustrates a block diagram of exemplary manners in which embodiments of the present invention may be stored, distributed and installed on a computer-readable medium.

FIG. 8 illustrates a block diagram of example manners in which embodiments of the present invention may be stored, distributed, and installed on a computer-readable medium. In FIG. 8, the "application" represents one or more of the methods and process operations discussed above. The application is initially generated and stored as source code 800 on a source computer-readable medium 802. The source code 800 is then conveyed over path 804 and processed by a compiler 806 to produce object code 808. The object code 808 is conveyed over path 810 and saved as one or more application masters on a master computer-readable medium 812. The object code 808 is then copied numerous times, as denoted by path 814, to produce production application copies 816 that are saved on separate production computer-readable media 818. The production computer-readable media 818 are then conveyed, as denoted by path 820, to various systems, devices, terminals and the like. A user terminal 822, a device 824 and a system 826 are shown as examples of hardware components, on which the production computer-readable medium 818 are installed as applications (as denoted by 828 through 832). For example, the production computer-readable medium 818 may be installed on the IMD 100 (shown in FIG. 1) and/or the microcontroller 520 (shown in FIG. 5). Examples of the source, master, and production computer-readable medium 802, 812, and 818 include, but are not limited to, CDROM, RAM, ROM, Flash memory, RAID drives, memory on a computer system, and the like. Examples of the paths 804, 810, 814, and 820 include, but are not limited to, network paths, the internet, Bluetooth, GSM, infrared wireless LANs, HIPERLAN, 3G, satellite, and the like. The paths 804, 810, 814, and 820 may also represent public or private carrier services that transport one or more physical copies of the source, master, or production computer-readable media 802, 812 or 818 between two geographic locations. The paths 804, 810, 814 and 820 may represent threads carried out by one or more processors in parallel. For example, one computer may hold the source code 800, compiler 806 and object code 808. Multiple computers may operate in parallel to produce the production application copies 816. The paths 804, 810, 814, and 820 may be intra-state, inter-state, intra-country, inter-country, intra-continental, inter-continental, and the like.

The operations noted in FIG. 8 may be performed in a widely distributed manner world-wide with only a portion thereof being performed in the United States. For example, the application source code 800 may be written in the United States and saved on a source computer-readable medium 802 in the United States, but transported to another country (corresponding to path 804) before compiling, copying and installation. Alternatively, the application source code 800 may be written in or outside of the United States, compiled at a compiler 806 located in the United States and saved on a master computer-readable medium 812 in the United States, but the object code 808 transported to another country (corresponding to path 814) before copying and installation. Alternatively, the application source code 800 and object code 808 may be produced in or outside of the United States, but production application copies 816 produced in or conveyed to the United States (for example, as part of a staging operation) before the production application copies 816 are installed on user terminals 822, devices 824, and/or systems 826 located in or outside the United States as applications 828 through 832.

As used throughout the specification and claims, the phrases "computer-readable medium" and "instructions configured to" shall refer to any one or all of (i) the source computer-readable medium 802 and source code 800, (ii) the master computer-readable medium and object code 808, (iii) the production computer-readable medium 818 and production application copies 816 and/or (iv) the applications 828 through 832 saved in memory in the terminal 822, device 824, and system 826.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for discriminating between cardiac signal waveforms using an implantable medical device, said method comprising:

sensing atrial waveforms of a heart and determining an atrial rate based on the atrial waveforms;

sensing ventricular waveforms of the heart and determining a ventricular rate based on first candidate waveforms and second candidate waveforms within the ventricular waveforms;

determining if the ventricular rate exceeds the atrial rate;

if the ventricular rate exceeds the atrial rate, comparing each of the first candidate waveforms of the ventricular waveforms and the second candidate waveforms of the ventricular waveforms to a first predetermined waveform template to obtain a first morphology indicator and a second morphology indicator, wherein the first and second morphology indicators represent a degree to which the respective first and second candidate waveforms match the first predetermined waveform template;

determining if the ventricular rate is correct, based on one or both of the first morphology indicator and the second morphology indicator;

if the ventricular rate is correct, applying therapy;

if the ventricular rate is incorrect, comparing the ventricular rate to the atrial rate to determine if the ventricular rate exceeds the atrial rate by a threshold amount; and if the ventricular rate exceeds the atrial rate by the threshold amount, inhibiting the application of therapy to the heart, otherwise applying therapy.

2. The method of claim 1, wherein the first predetermined waveform template is representative of a QRS complex, and the ventricular rate is determined to be correct when the first morphology indicator indicates that the first candidate waveform matches the first predetermined waveform template and the second morphology indicator indicates that the second candidate waveform does not match the first predetermined waveform template.

3. The method of claim 1, wherein the first predetermined waveform template is representative of a T-wave, and the ventricular rate is determined to be incorrect when the first morphology indicator indicates that the first candidate waveform matches the first predetermined waveform template or the second morphology indicator indicates that the second candidate waveform matches the first predetermined waveform template.

4. The method of claim 1, wherein the comparing operation includes calculating a first area of the first candidate waveform with respect to a baseline, calculating a second area of the second candidate waveform with respect to the baseline and comparing each of the first and second areas to an area of the waveform template.

5. The method of claim 1, wherein the comparing operation comprises calculating an area of a fragment of the first candidate waveform with respect to a baseline, calculating an area of a fragment of the second candidate waveform with respect to the baseline, and comparing the areas of the fragment of each of the first and second candidate waveforms with an area of a fragment of the predetermined waveform template.

6. An implantable medical device for discriminating between cardiac signal waveforms, said device comprising:

electrodes configured to be positioned proximate to a heart for sensing atrial waveforms of a heart and ventricular waveforms of the heart having first candidate waveforms and second candidate waveforms; and a microcontroller configured to:

determine an atrial rate based on the atrial waveforms, determine a ventricular rate based on the first candidate waveforms and the second candidate waveforms within the ventricular waveforms, and determine of the ventricular rate exceeds the atrial rate;

if the ventricular rate exceeds the atrial rate, compare each of the first candidate waveforms of the ventricular waveforms and the second candidate waveforms of the ventricular waveforms to a first predetermined waveform template to obtain a first morphology indicator and a second morphology indicator, wherein the first and second morphology indicators represent a degree to which the respective first and second candidate waveforms match the first predetermined waveform template;

determine if the ventricular rate is correct, based on one or both of the first morphology indicator and the second morphology indicator;

apply therapy if the ventricular rate is correct;

if the ventricular rate is incorrect, compare the ventricular rate to the atrial rate to determine if the ventricular rate exceeds the atrial rate by a threshold amount; and if the ventricular rate exceeds the atrial rate by the threshold amount, inhibit the application of therapy to the heart, otherwise apply therapy.

7. The device of claim 6, further comprising an excitation source for applying therapy to the heart, wherein the first predetermined waveform template is representative of a QRS complex and the microcontroller determines the ventricular rate is incorrect when the first morphology indicator indicates that the first candidate waveform matches the first predetermined waveform template and the second morphology indicator indicates that the second candidate waveform does not match to the first predetermined waveform template.

8. The device of claim 6, further comprising an excitation source for applying therapy to the heart, wherein the first predetermined waveform template is representative of a T-wave and the microcontroller determines the ventricular rate is incorrect when the first morphology indicator indicates that the first candidate waveform matches the first predetermined waveform template or the second morphology indicator indicates that the second candidate waveform matches to the first predetermined waveform template.

* * * * *